United States Patent [19]

Zito

[11] Patent Number: 4,999,512
[45] Date of Patent: Mar. 12, 1991

[54] OPTICAL POWDER IMPURITY DETECTOR

[76] Inventor: Richard R. Zito, 330 N. Mathilda Ave. (#606), Sunnyvale, Calif. 94086

[21] Appl. No.: 445,418

[22] Filed: Dec. 4, 1989

[51] Int. Cl.⁵ ............................................. G01N 15/06
[52] U.S. Cl. .................................... 250/574; 356/336
[58] Field of Search ............... 250/574, 576, 564, 565; 356/336, 337, 338, 340, 341, 343

[56] References Cited

U.S. PATENT DOCUMENTS

| | | | |
|---|---|---|---|
| 3,819,269 | 6/1974 | Duvall et al. ......................... | 356/336 |
| 3,901,602 | 8/1975 | Gravatt ................................ | 250/574 |
| 4,728,190 | 3/1988 | Knollenberg ....................... | 356/338 |
| 4,917,496 | 4/1990 | Sommer ............................. | 356/336 |

Primary Examiner—David C. Nelms

[57] ABSTRACT

An optical method of detecting impurities in powders. The detector employs a laser (10) as a source of radiation which impinges upon a stream of powder and impurities as they are blown through a clear glass tube (14). The scattered radiation then stimulates photoresistors (18) so as to produce a signal which can be displayed and recorded on a chart recorder or computer display device (26).

4 Claims, 2 Drawing Sheets

OPTICAL POWDER IMPURITY DETECTOR

BACKGROUND—FIELD OF INVENTION

This invention relates to the detection of impurities in powders by optical methods.

BACKGROUND—DESCRIPTION OF PRIOR ART

It is frequently required to identify particulate impurities in powders. This type of identification is particularly common in the food processing industry. For example, it may be desirable to identify the number of insect fragments in a ground up spice such as paprika. The traditional method for performing such an analysis is to digest a powder like paprika in chemicals which leave the more inert chitin and chitin-like parts of the insect exoskeleton behind (e.g. see W. Horwitz, "Official Methods of Analysis of the Association of Official Analytical Chemists," thirteenth Ed., 1980 pp. 806-810; also see H. C. B. Grzimek, "Animal Life Encyclopedia-Vol. 1, "Van Nostrand, 1972, pp. 397-398). This method of analysis leaves much to be desired because it is wet, slow expensive, labor intensive, and does not monitor the product in a continuous, on-line, real-time way.

This patent application describes an optical method of analysis which overcomes the previously mentioned limitations. The U.S. Pat. No. 3,901,602 to Gravatt (1975) also describes an optical apparatus which is potentially capable of characterizing the constituents of mixtures of particles by means of light scattering. The Gravatt device was intended to be used as a smoke detector capable of detecting fire-produced aerosols without interference from non-fire-produced aerosols. Gravatt employs an incandescent or medium pressure mercury arc lamp as a light source. Lenses are also employed to collect, collimate, and concentrate light from the source. Two diaphragms are also employed for collimation. Finally, a linear polarizer is used to polarize the light from the source. Next, light prepared in this way falls upon a stream of particles flowing through a flow tube and, after scattering, the radiation is collected via a cone shaped aperture and is concentrated onto a detector by means of another lens. By comparison, instead of a lamp, my invention uses an inexpensive, low power, unpolarized, laser light source with a two year continuous operation lifetime. Laser light is automatically collimated and concentrated so that all the lenses, collimators, and diaphragms are eliminated. Even the concentrating lens at the detector has been eliminated by the use of rugged high sensitivity CdS photoresistors as optical detectors. Furthermore, my device can operate with unpolarized light so that the polarizers can also be eliminated. These simplifications make my device more inexpensive, more rugged, more reliable, and easier to maintain. Furthermore, the Gravatt apparatus uses only radiation scattered into an angular range from 30 to 90 degrees of the incident direction. Since my primary application was unanticipated by Gravatt, radiation scattered into this angular range is not of interest and is therefore not collected and analyzed in my device. My primary, but not exclusive, application (i.e. detection of powdered impurities in powdered foods) demands inspection of radiation scattered into the zero to 30 degree angular range, including radiation scattered out of the plane defined by the incident beam and the sample flow tube which carries the powdered sample. The most efficient detection operation employs collection of unpolarized light at about 18 degrees to the incident direction. The Gravatt device shows the sample flow tube tipped at a non-perpendicular angle to the incident beam. For my application the sample flow tube should be as close to perpendicular to the incident beam as possible for the best performance. Finally, Gravatt has not anticipated the need for a dust-proof and light-proof enclosure for his apparatus. Without such an enclosure, room lights and light scattering from floating dust will interfere with the operation of the detector. This effect will be described in more detail in later sections. It is doubtful that the Gravatt device, as described in his diagrams and application, can work in any realistic non-laboratory setting without such an enclosure.

OBJECTS AND ADVANTAGES

Acordingly, the several objects and advantages of the present invention are:

(a) to provide an optical impurity detector which is capable of efficiently detecting powdered impurities, and distinguishing such fragments from normal pure powder materials;

(b) to provide an optical impurity detector which is safe, not labor intensive, reliable, inexpensive, and is easy to maintain and operate;

(c) to provide an optical impurity detector which can be easily introduced into the production line (i.e. can be easily used with powders);

(d) to provide real-time on-line detection of impurities in powders; and (e) to provide an optical impurity detector which is not affected by airborne dust and ambient light.

Further objects and advantages will become apparent from a consideration of the ensuing description and drawings.

DRAWING FIGURES

Figure 1:
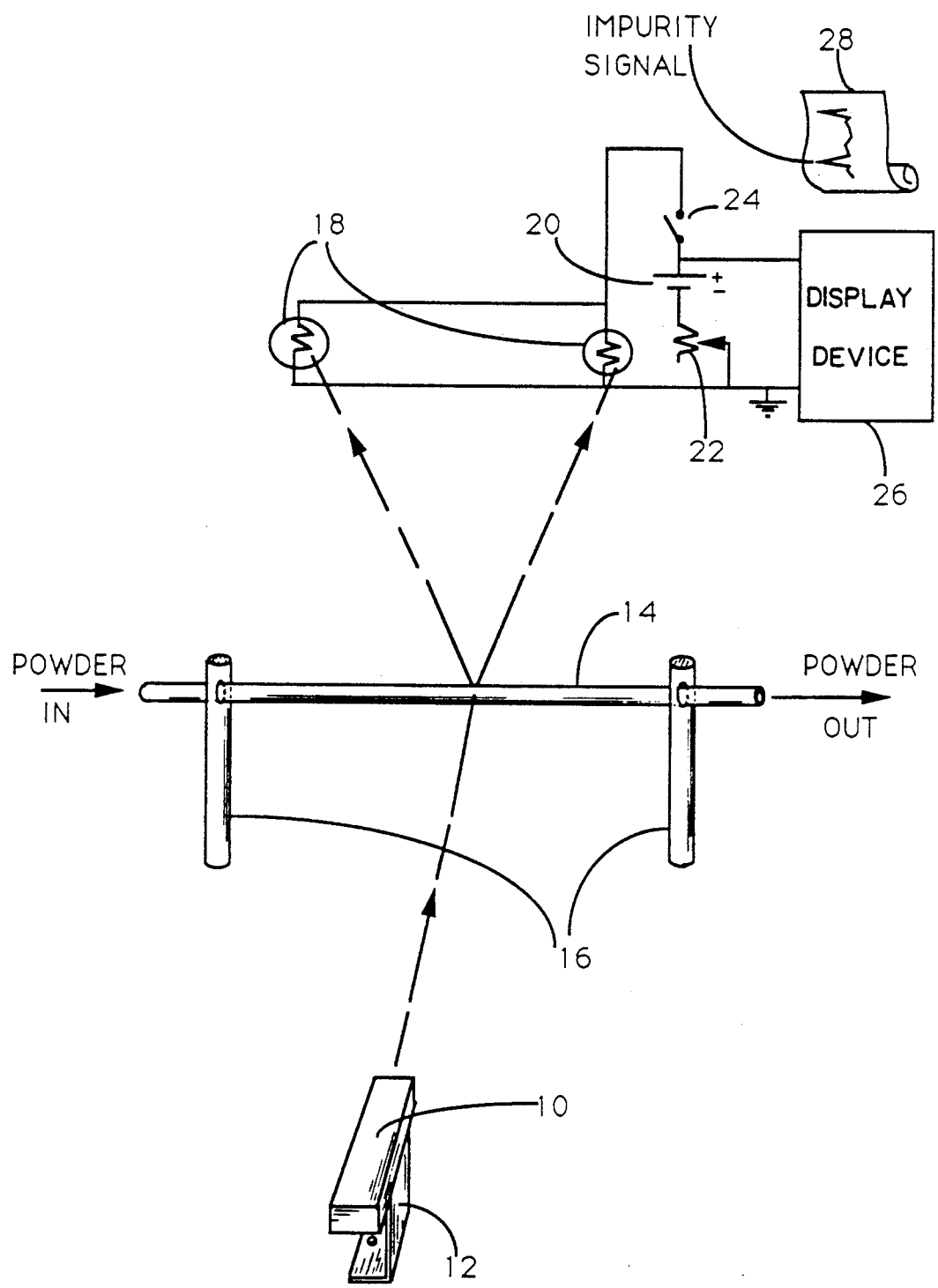
FIG. 1 shows the arrangement and interconnection of optical, optoelectronic and electronic components of the powder impurity detector.

REFERENCE NUMERALS IN DRAWING 10 laser
12 mounting bracket
14 transparent glass tube
16 ridged supports
18 photoresistors
20 voltage source
22 potentiometer
24 switch
26 display device
28 output chart
30 enclosure with a latching door
32 seal
34 black insulated wires
36 black housing
38 multiconductor ribbon
40 legs

DESCRIPTION—FIGS. 1 AND 2

Figure 2:
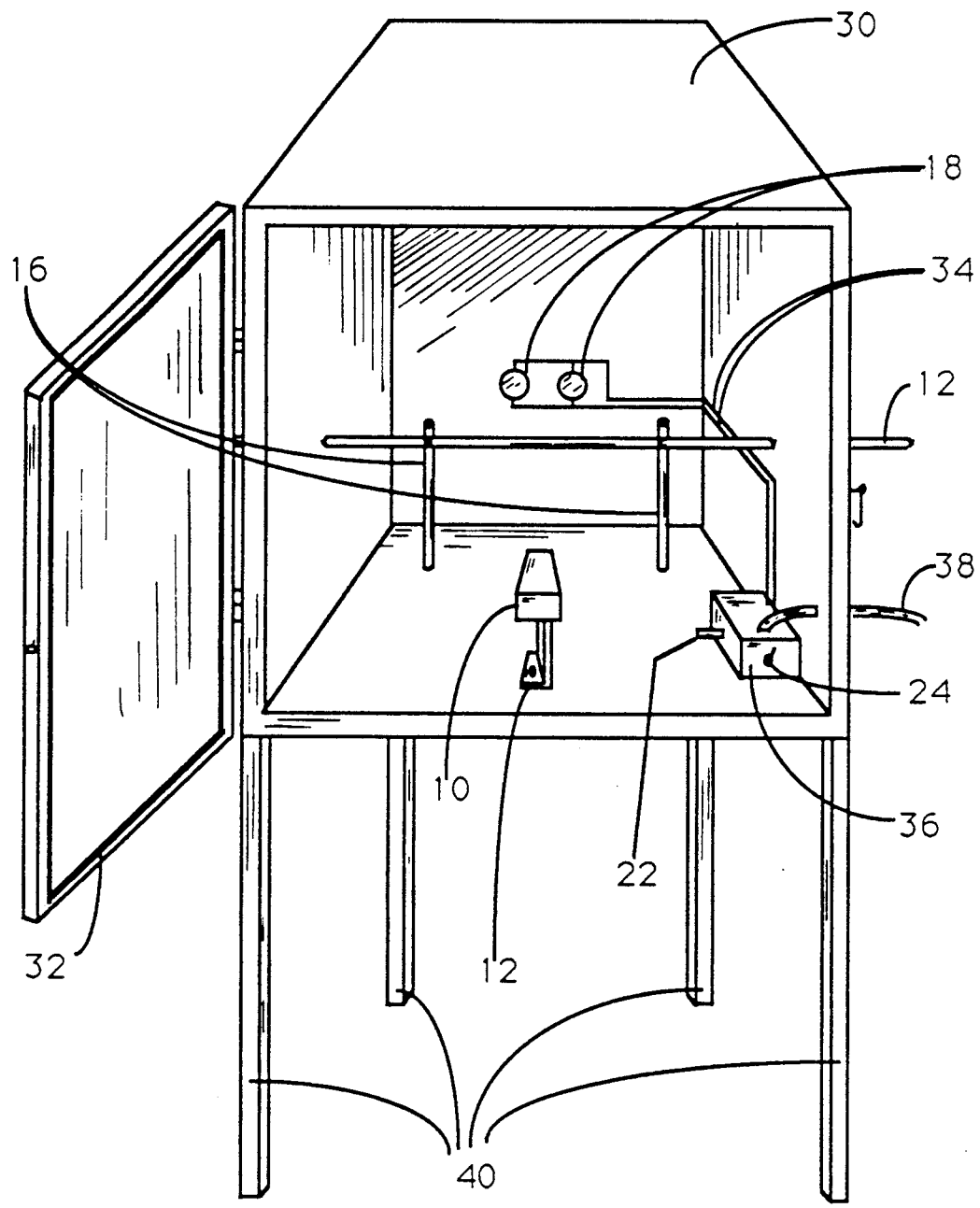
FIG. 2 shows a light-proof and dust-proof enclosure within which most of the components are contained.

A typical embodiment of the optical powder impurity detector is illustrated by the components of FIG. 1 and the surrounding enclosure of FIG. 2. Referring to FIG.

1, the radiation source is a laser 10 which is typically of the He-Ne or He-Cd type with an output power of about 0.5 milliwatts. However, the laser radiation sourcce need not be limited to these types. The laser is conveniently attached to a mounting bracket 12. The use of a proper height mounting bracket 12 allows the height of the laser beam to be adjusted for proper alignment. Next, the emitted radiation from the laser passes through glass tube 14 which carries the powder to be inspected in a high speed fluid (gas or liquid) flow typically having a velocity of about 20 meters per second. Glass tube 14 need not be polished. This type of inspection is particularly convenient since powders, such as those used by the food processing industry, are normally transported from point to point in the processing and packaging sequence by being blown through tubes. Glass tube 14 is held in place by two ridged supports 16. Radiation scattered from powder particles and impurities may then strike one or more photoresistors 18 which act as optical radiation detectors. Typically, photoresistors of the CdS type, whose dark resistance exceeds about 20 million ohms and whose room light resistance is about 1750 ohms, can be used, but other types of photoresistors will also work and are acceptable replacements. In the preferred embodiment, two photoresistors are used and are spaced along the length of glass tube 14 so that the optical path connecting the center of each photoresistor to the point of impact of the incident laser beam on the glass tube makes an angle of about 18 degrees with the incident direction. In other words, the cells are placed so as to capture radiation scattered into a direction which deviates from the original beam heading by about 18 degrees. Other embodiments include one or more photoresistors placed at various locations around glass tube 14. The location being experimentally determined so as to provide the largest signals during detection of impurity fragments. The photoresistors are powered by a voltage source 20 which is usually, but not necessarily, a 9 volt battery. Other acceptable voltage sources include, for example, an alternating current power supply whose voltage has been reduced from the usual household 110 volts by a step-down transformer. the new, lower voltage can then be rectified and filtered for use. The actual signal to be recorded and used for analysis is a voltage which is measured across a potentiometer 22. Typically, potentiometer 22 has a maximum resistance of 1000 ohms and a linear taper. However, other types of potentiometers may be used which have a different maximum resistance, or a non-linear taper, or both. A switch 24 allows the power to the apparatus to be turned off thus conserving the energy of voltage source 20. Voltages across potentiometer 22 are recorded and displayed on a display device 26, which typically may be, but is not limited to, a personal computer with an analogue to digital measurement capability or a chart recorder. In the preferred embodiment a computer is used because data can be numerically analyzed as it is received, and displayed in any number of meaningful ways. A great variety of software is commercially available for analysis of voltage signals collected by computer. In addition, other embodiments of the powder impurity detector might employ a digital to analogue converter so that under suitable conditions signals could be sent from the computer to, say, close a valve so as to prevent contaminated powders from being processed. Finally, the collected signals may be recorded on a hardcopy output chart 28.

All of the components described above, except display device 26 and output chart 28, are contained within a light-proof and dust-proof enclosure with a latching door 30 shown in FIG. 2. Around the edge of the door is a light-proof and dust-proof seal 32 which is typically made from the adhesive backed weather stripping commonly available in hardware stores for sealing household doors against the elements. Other types of seals, such as O-rings, can also be used. Enclosure 30 is typically made of aluminum, steel, or wood and is painted on the interior with light absorbing flat black paint. The ends of tube 14 penetrate through the side panels of enclosure 30 and these ends are also painted with light absorbing flat black paint on their outside surface. Mounting bracket 12 and ridged supports 16 are both attached to the bottom panel on the interior of enclosure 30 as shown in FIG. 2. Photoresistors 18 may be attached to the back panel on the interior of enclosure 30 with silicone rubber adhesive. Black insulated wires 34 carry current to electronic components contained within black housing 36. Voltage source 20 is also contained within black housing 36. Communication between the components contained within black housing 36 and display device 26 is achieved by a flexible multiconductor ribbon 38 which passes through the side of enclosure 30. If only two photoresistors 18 are used as in FIG. 1, then only two conductors of multiconductor ribbon 38 will be in use. If a more complex photoresistors array is employed, then all the individual conductors of multiconductor ribbon 38 may be used. Thus, display device 26 may be placed on a desk or any other convenient spot. The entire apparatus (except for the display device) is supported at an appropriate height for any particular application by a set of legs 40.

OPERATION—FIGS. 1 AND 2

The operation of the powder impurity detector is based on the principle that the light scattering properties of impurities are often very different from those of the pure powder particles. The detection of insect fragments in a spice like paprika provides a good example. The carbohydrate chitin, which is an important constituent of insect exoskeletons, is quite reflective. If a piece of chitin flies through a laser beam emitted from laser 10, light will be scattered via a reflection process into new directions, different from that of the incident beam, with high efficiency. If a bright reflection strikes a photoresistor (such as one of the photoresistors 18) its electrical resistance will drop dramatically. Therefore, if switch 24 is closed so that current can flow from voltage source 20, a large voltage drop will appear across potentiometer 22. By comparison, a complex, irregularly shaped, non-specular paprika grain will scatter a relatively low level of optical intensity in all directions more or less uniformly, thereby making only a small reduction in resistance at photoresistors 18. If the resistance of photoresistors 18 remains high, then the voltage drop across photoresistors 18 will be large and that across potentiometer 22 will be relatively small. Therefore, chitin fragments passing through the laser beam produce voltage spikes which can be displayed and recorded on display device 26, or stored as hard copy on output chart 28. Of course, not every chitin fragment will result in a spike since some reflections might head in a direction which misses a photoresistor. However, some fragments will create voltage spikes, and the total number of such spikes per unit time will be proportional to the impurity concentration measured in the number of fragments per unit volume of paprika. If the impurity to be detected is, for example, a hair in paprika powder, then the operant mechanism which scatters light into the photoresistors is fiber diffractions instead of reflection. Nevertheless, the operation of the system is the same, with the hair impurity producing a spike which registers on display device 26.

Finally, it should be noted that under normal factory conditions the optical powder impurity detector would be enclosed in a dark dust proof enclosure 30 whose interior has been painted with light absorbing flat back paint. Such an enclosure prevents reduction of the resistance of photoresistors 18 by room lights and other factory lighting external to the device. Only the ends of glass tube 14 would penetrate through the sides of the enclosure. Experiments have shown that the light leakage into the enclosure at these penetration points is insufficient to create false signals, provided the ends of glass tube 14 which lie outside the enclosure are blackened on their outside surface. An enclosure also prevents irrelevant particles of airborne factory dust outside glass tube 14 from inadvertently scattering radiation to photoresistors 18 and creating a false signal.

In conclusion, it should be noted that the mechanisms involved in the optical detection of impurities are still under investigation and I do not wise to be bound by any of the mechanisms described in this application.

SUMMARY, RAMIFICATION, AND SCOPE

Accordingly, the reader will see that the optical powder impurity detector is easy to introduce into the production line for real-time detection of impurities since powders are normally blown through tubes during routine factory processing. If impurities become too numerous, the starting materials being feed into the production line input can be exchanged for cleaner starting materials. Furthermore, since the optical powder impurity detector contains only inexpensive non-moving parts, the mechanism is highly reliable, easy to maintain, and inexpensive.

Although the description above contains many specificities, these should not be construed as limiting the scope of the invention, but as merely providing illustrations of some presently preferred embodiments and uses of this invention. For example, the optical powder impurity detector can be used to detect other types of impurities such as tiny metal fragments or abrasives in powders such as flour, black pepper, oregano, cinnamon, cocoa, powdered graphite lubricant, tooth powder, baking soda, and very fine polishing agents, etc. Powders can be examined with incident radiation that is unpolarized, linearly polarized, or circularly polarized. Linearly polarized light can have its plane of polarization parallel to, or tipped at 45 degrees to, the plane defined by the incident beam and the powder stream (passing through glass tube 14). Similarly, for any given type of incident radiation just described, radiation detection can involve measurement of the total scattered intensity (regardless of polarization), or the intensity of just the parallel or 45 degree plane polarized components of the scattered radiation, or the intensity of just the circularly polarized component. Also, the number, type, and placement of detectors can be varied. Radiation can be collected at any angle about glass tube 14 including the backscatter directions and directions out of the plane defined by the incident beam and glass tube 14. The glass tube 14 can be made of a transparent plastic, polished quartz, or other transparent crystalline, noncrystalline, or polymeric materials. Electronic circuitry may contain amplifiers to boost voltage signal peaks and/or a zener diode or other voltage regulator to make sure voltage peaks don't get too large for the computer's (display device 26) analogue to digital converter. Another trivial variation on the basic scheme is to display a current signal, instead of a voltage signal, on display device 26, or to measure the resistance of the photoresistors directly. Finally, the potentiometer 22 could be replaced by a fixed resistor and a variety of possible display devices could be used other than a computer or chart recorder.

Thus, the scope of the invention should be determined by the appended claims and their legal equivalents, rather than by the examples given.

I claim:

1. A powder impurity detector, comprising:
   (a) a transparent tube which carries an impurity contaminated powder in a high speed flowing fluid,
   (b) a laser, which acts as a sourced of collimated radiation, so that said radiation can pass through said transparent tube,
   (c) an electrical means for detecting said radiation that is scattered by particles of said impurity contaminated powder,
   (d) a display and recording device so that signals produced by said electrical means can be analyzed,
   (e) a light-proof and dust-proof enclosure for all components, except said display and recording device, which prevents unwanted sources of radiation and dust from interfering with signals produced by said electrical means,
   (f) a digital to analogue convertor so that under suitable conditions signals can be sent from said display and recording device to prevent the contaminated powders from being processed.

2. The invention of claim 1 wherein said electrical means consists of two photoresistors placed so as to capture the radiation scattered into a direction which deviates from the original beam heading by about 18 degrees and each said photoresistor is attached to the back panel on the interior of said enclosure.

3. A powder impurity detector, comprising:
   (a) a transparent tube which carries an impurity contaminated powder in a high speed flowing fluid,
   (b) a laser, which acts as a source of collimated radiation, so that said radiation can pass through said transparent tube,
   (c) a light-proof and dust-proof enclosure which prevents unwanted sources of radiation and dust from interfering with said radiation passing through said transparent tube,
   (d) two photoresistors for detecting the optical radiation, each said photoresistor being places so as to capture radiation scattered into a direction which deviates from the original beam heading by about 18 degrees and each said photoresistor is attached to the back panel on the interior of said enclosure,
   (e) a display and recording device so that said radiation scatterred from impurities and powder particles in said transparent tube may be analyzed.

4. The invention of claim 2 further including a digital to analogue converter so that under suitable conditions signals can be sent from said display and recording device to prevent the contaminated powders from being processed.

* * * * *